United States Patent [19]

Wang et al.

[11] 4,012,466
[45] Mar. 15, 1977

[54] PRODUCTION OF 5,5-BIS(HALOMETHYL)-1,3,2-DIOXA-PHOSPHORINANES

[75] Inventors: Richard H. S. Wang; James G. Pacifici, both of Kingsport, Tenn.

[73] Assignee: Eastman Kodak Company, Rochester, N.Y.

[22] Filed: Dec. 1, 1975

[21] Appl. No.: 636,390

[52] U.S. Cl. .............................. 260/974; 260/937
[51] Int. Cl.² .......................................... C07F 9/09
[58] Field of Search ................... 260/974, 937, 975

[56] References Cited

UNITED STATES PATENTS

| | | | |
|---|---|---|---|
| 3,887,655 | 6/1975 | Shim | 260/937 |
| 3,890,409 | 6/1975 | Mayerhoefer et al. | 260/937 X |

Primary Examiner—Richard L. Raymond
Attorney, Agent, or Firm—Elliott Stern; Daniel B. Reece, III

[57] ABSTRACT

This invention relates to a process for the preparation of 5,5-bis(halomethyl)-1,3,2-dioxa-phosphorinanes from a dihaloneopentyl glycol and a phosphorous oxyhalide in the presence of a hydrogen chloride accepting reagent. These compounds are useful as flame retardants for polyesters.

4 Claims, No Drawings

PRODUCTION OF 5,5-BIS(HALOMETHYL)-1,3,2-DIOXA-PHOSPHORINANES

This invention relates to a method for producing 5,5-bis(halomethyl)-1,3,2-dioxa-phosphorinanes from dihaloneopentyl glycols and phosphorous oxyhalides. These compounds are useful as flame retardants which are exceptionally effective in polyesters. See for example U.K. Pat. No. 1,371,212.

Accordingly, there is provided a process for the preparation of 5,5-bis(halomethyl)-1,3,2-dioxa-phosphorinanes having the formula

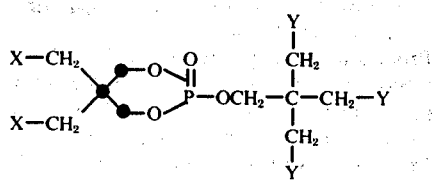

wherein X is chloro or bromo, and each Y is the same or different and represents chloro or bromo, which comprises reacting at least about 1.5 mole proportions of dichloroneopentyl glycol or dibromoneopentyl glycol with one mole proportion of phosphorous oxychloride or phosphorous oxybromide in the presence of a hydrogen chloride accepting reagent at a temperature of from about 40° C. to 180° C.

The compounds prepared according to this invention are obtained in high yields. The reaction is conveniently carried out at temperatures which are sufficient to produce the desired phosphorinane but insufficient to decompose the product. These results are achieved by conducting the process at a temperature within the range of 40° to about 180° C. and preferably from 80° to about 170° C. Of course, the preferred or optimum temperature varies between these ranges depending upon the specific reagents employed. The time required to complete the reaction will vary with the reactions, however, it has been found that periods of greater than 1 hour are usually sufficient to complete the reaction preferably at least about 4 hours.

Generally, the process may be conducted under standard atmospheric pressure in an atmosphere of nitrogen although subatmospheric or superatmospheric pressure can also be used.

The reaction is generally carried out using about 1.5 mole proportions of glycol to 1 mole proportion of phosphorous oxyhalide although greater amounts of glycol can be utilized. Preferably, however, from 1.5 to about 4 moles of glycol should be utilized.

In accordance with this invention it is necessary that the reaction be carried out in the presence of a hydrogen chloride accepting reagent such as triethylamine, pyridine, N,N-dimethyl aniline, the alkali metal carbonates, bicarbonates, or acetates, aluminum oxide, barium oxide, calcium hydroxide, calcium oxide, etc. Furthermore, it has been found advantageous to run the above reaction in the presence of a solvent which is inert to the reagents and the products. This solvent should have a boiling point of between about 40° and 180° C. Especially preferred of these solvents are the aromatic solvents such as dichlorobenzene, toluene, xylene, tetrachloroethylene, as well as the hydroxylic solvents such as ethylene glycol and methyl cellusolve.

After the reaction is completed, which usually takes from about 1 hour to about 15 hours, the reaction mixture is allowed to cool to room temperature and it then may be poured into ice water and then filtered or extracted with ethanol, water or any other suitable solvent. The following examples are included for a better understanding of this invention.

EXAMPLE 1

A mixture of dibromoneopentyl glycol (0.03 mole), phosphorous oxychloride (0.015 mole), and pyridine (0.06 mole) in 100 ml. of tetrachloroethylene was refluxed for 2 hr. After 200 ml. of ice water was added to the reaction mixture, the product, I, was obtained by filtration and recrystallization from ethanol-water (m.p. 130°–5°, 50% yield).

Anal. Found for I, $C_{10}H_{16}Br_3Cl_2O_4P$ (Calcd): C 23.0 (22.1); H 3.1 (3.0); Br 41.13 (44.3); Cl 14.62 (13.1); P 6.0 (5.7).

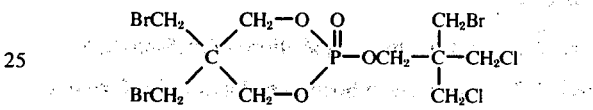

I

EXAMPLE 2

A mixture of dibromoneopentyl glycol (0.06 mole), phosphorus oxychloride (0.04 mole), and pyridine (0.12 mole) in 120 ml. of toluene was refluxed for 6 hr. After the reaction mixture was processed as described in Example 1, the Mixture A products I and II was obtained (m.p. 128°–130°, 50% yield).

Anal. Found for mixture of I and II, $C_{20}H_{32}Br_5Cl_5O_8P_2$ (Calcd): C 23.70 (23.09); H 3.14 (3.08); Br 37.42 (38.48); Cl 17.09 (17.08); P 5.91 (5.96).

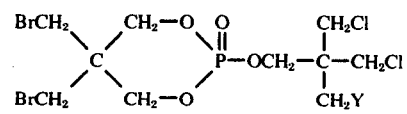

I (Y=Br, 50%) and II (Y=Cl, 50%)

EXAMPLE 3

A mixture of dibromoneopentyl glycol (0.02 mole), phosphorus oxychloride (0.01 mole), and pyridine (0.03 mole) in 100 ml. of toluene was refluxed for 15 hr. After the reaction mixture was processed as described in Example 1, the mixture of products I and III was obtained (m.p. 137°–140°, 50% yield).

Anal. Found for mixture of I and III, $C_{20}H_{32}Br_7Cl_3O_8P_2$ (Calcd): C 21.64 (21.10); H 3.04 (2.81); Br 48.94 (50.64); Cl 8.63 (8.74); P 5.61 (5.45).

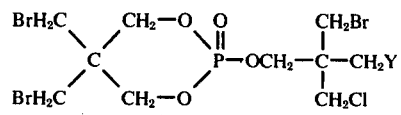

I (Y=Cl, 60%) and III (Y=Br, 40%)

EXAMPLE 4

A sample (100 g.) of poly(ethylene terephthalate) powder was dry mixed with 10 g. of the composition prepared as in Example 1. This mixture was molded into 10-mil film and the oxygen index determined. A value of 24.1 was obtained for the sample containing the additive, whereas the sample containing no additive had an oxygen index of 19.0.

The invention has been described in detail with particular reference to preferred embodiments thereof, but it will be understood that variations and modifications can be effected within the spirit and scope of the invention.

We claim:

1. Process for the preparation of 5,5-bis(halomethyl)-1,3,2-dioxa-phosphorinanes having the formula

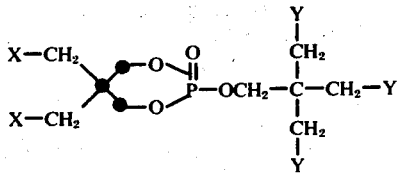

wherein X is chloro or bromo, and each Y is the same or different and represents chloro or bromo, which comprises reacting at least about 1.5 mole proportions of dichloroneopentyl glycol or dibromoneopentyl glycol with one mole proportions of phosphorous oxychloride or phosphorous oxybromide in the presence of a hydrogen chloride accepting reagent at a temperature of from about 40° to about 180° C.

2. Process according to claim 1 wherein the reactants are dibromoneopentyl glycol and phosphorous oxychloride and the reaction is carried out at a temperature of from about 80° to abut 170° C.

3. Process according to claim 1 wherein the hydrogen chloride accepting reagent is pyridine.

4. Process according to claim 2 wherein the hydrogen chloride accepting reagent is pyridine.

* * * * *